United States Patent
Shioiri (10) Patent No.: US 10,543,059 B2
(45) Date of Patent: Jan. 28, 2020

(54) METHOD OF PRODUCING A MEDICAL CUTTING TOOL

(71) Applicant: Mutsunori Shioiri, Utsunomiya (JP)

(72) Inventor: Mutsunori Shioiri, Utsunomiya (JP)

(73) Assignee: MANI, INC., Utsunomiya-Shi Tochigi (JP)

( * ) Notice: Subject to any disclaimer, the term of this patent is extended or adjusted under 35 U.S.C. 154(b) by 197 days.

(21) Appl. No.: 15/835,255

(22) Filed: Dec. 7, 2017

(65) Prior Publication Data
US 2019/0008609 A1    Jan. 10, 2019

Related U.S. Application Data

(62) Division of application No. 13/813,399, filed as application No. PCT/JP2011/067263 on Jul. 28, 2011, now abandoned.

(30) Foreign Application Priority Data

Jul. 3, 2010    (JP) .................................. 2010-171777

(51) Int. Cl.
    *B23K 31/02*    (2006.01)
    *A61C 3/02*     (2006.01)
    (Continued)

(52) U.S. Cl.
    CPC ................ *A61C 3/02* (2013.01); *A61B 17/16* (2013.01); *B23K 1/0008* (2013.01); *A61B 2017/00526* (2013.01); *B23K 2101/20* (2018.08)

(58) Field of Classification Search
    CPC . A61C 3/02; A61B 17/16; A61B 2017/00526; B23K 1/00–206;
    (Continued)

(56) References Cited

U.S. PATENT DOCUMENTS

| 4,834,655 | A | * | 5/1989 | Kyotani | ................... | A61C 3/02 433/166 |
| 5,816,807 | A | | 10/1998 | Matsutani et al. | | |

(Continued)

FOREIGN PATENT DOCUMENTS

| EP | 2174616 A1 | * | 4/2010 | ............... A61C 3/02 |
| EP | 2174616 A1 | | 4/2010 | |

(Continued)

OTHER PUBLICATIONS

International Search Report directed to International Patent Application No. PCT/JP2011/067263, 4 pages including English translation.

(Continued)

*Primary Examiner* — Kiley S Stoner
(74) *Attorney, Agent, or Firm* — Shlesinger, Arkwright & Garvey LLP (57) ABSTRACT

Method of producing a medical cutting tool and a medical cutting tool that will not rust and that is capable of stably demonstrating high strength. A working section formed by a cemented carbide or ceramic is brazed to the tip of a shank part formed by a round bar-shaped austenitic stainless steel, thereby constituting a cutting tool. The shank part includes a shank, a neck, and a joint to which the working section is brazed. At least part of the stainless steel near the joint of the neck and in the joint has a fiber-like structure. The structure of the stainless steel in the joint on the working section side has a granular structure.

8 Claims, 6 Drawing Sheets

(51) Int. Cl.
*A61B 17/16* (2006.01)
*B23K 1/00* (2006.01)
*A61B 17/00* (2006.01)
*B23K 101/20* (2006.01)

(58) Field of Classification Search
CPC ...... B23K 2101/20; B23K 2103/04–05; B23K 2103/52; B23K 2103/16; B23K 2103/166; B23K 2103/172
USPC ................ 228/173.1, 173.3–173.5, 245–262
See application file for complete search history.

(56) References Cited

U.S. PATENT DOCUMENTS

| | | | | |
|---|---|---|---|---|
| 6,116,360 | A * | 9/2000 | Evans | E21B 10/54 175/371 |
| 6,257,889 | B1 * | 7/2001 | Boston | A61C 3/02 433/165 |
| 7,232,311 | B1 * | 6/2007 | Greggs | A61C 3/02 433/165 |
| 2002/0037490 | A1 * | 3/2002 | Oyamada | A61C 3/02 433/165 |
| 2004/0018468 | A1 * | 1/2004 | Gorokhovsky | A61B 17/1615 433/166 |
| 2004/0063068 | A1 * | 4/2004 | Ikushima | A61C 3/02 433/165 |
| 2004/0081940 | A1 * | 4/2004 | Roetzer | A61C 3/02 433/165 |
| 2004/0152045 | A1 * | 8/2004 | Kachalon | A61C 3/02 433/165 |
| 2006/0105293 | A1 * | 5/2006 | Funato | A61C 3/02 433/165 |
| 2006/0286506 | A1 * | 12/2006 | Birnholtz | A61C 3/02 433/165 |
| 2007/0015107 | A1 | 1/2007 | Mannschedel et al. | 433/102 |
| 2007/0151554 | A1 * | 7/2007 | Song | B23D 61/18 125/15 |
| 2007/0298376 | A1 * | 12/2007 | Kmiecz | A61B 17/1615 433/165 |
| 2009/0039117 | A1 | 2/2009 | Mashiko | A61B 17/06066 223/102 |
| 2009/0170053 | A1 * | 7/2009 | Ikemi | A61C 3/02 433/166 |
| 2010/0023054 | A1 * | 1/2010 | Matsutani | A61B 17/06066 606/223 |
| 2010/0069956 | A1 * | 3/2010 | Matsutani | A61B 17/06066 606/222 |
| 2011/0195377 | A1 * | 8/2011 | Sun | A61C 3/02 433/165 |
| 2012/0165851 | A1 * | 6/2012 | Murakami | A61B 17/3421 606/185 |
| 2013/0029288 | A1 * | 1/2013 | Novak | A61C 1/141 433/127 |
| 2013/0171583 | A1 * | 7/2013 | Shioiri | A61C 3/02 433/144 |
| 2013/0172917 | A1 * | 7/2013 | Saito | A61B 17/3211 606/167 |
| 2013/0197549 | A1 * | 8/2013 | Kato | A61B 17/06066 606/167 |
| 2013/0302748 | A1 * | 11/2013 | Friedrichs | A61C 1/055 433/82 |

FOREIGN PATENT DOCUMENTS

| | | | |
|---|---|---|---|
| JP | 06-199580 A | 7/1994 | |
| JP | 08-206133 A1 | 8/1996 | |
| JP | 09-075373 A | 3/1997 | |
| JP | 2010-120144 A | 6/2010 | |
| JP | 2011172786 A * | 9/2011 | ....... A61B 17/06066 |
| WO | 2007/135936 A1 | 11/2007 | |
| WO | 2009/017148 A1 | 2/2009 | |
| WO | 2009/107595 A1 | 9/2009 | |
| WO | WO 2009/107595 | 9/2009 | |

OTHER PUBLICATIONS

Translation of Mani et al. WO 2009/107595 through Sehreiber Translations.
Effect of Rolling and Annealing on Hardness of Brass, pp. 1-5, Andrew Cantrell, University of Washington, Edmonds Community College; Seattle, Washington; 2009.
"Joining Stainless Steel by by soldering, brazing, and resistance welding" by L.D. Connell reprint from Stainless Steel Industry of Jan. 1975.
Machine Translation of 2009 publication of Mani et al. WO 2009/107595 from World Intellectual Property Association website.

* cited by examiner

METHOD OF PRODUCING A MEDICAL CUTTING TOOL

CROSS-REFERENCE TO RELATED APPLICATIONS

This application is a Divisional application of application Ser. No. 13/813,399, filed Jan. 30, 2013, which is a 371 National Stage application of application No. PCT/JP2011/067263, filed Jul. 28, 2011, and which claims the priority of Japanese application No. JP 2010-171777, filed Jul. 3, 2010, and each of which is incorporated herein by reference.

TECHNICAL FIELD

The present invention relates to a medical cutting tool which is used to cut a surface layer of a tooth, a bone including an alveolar bone, and the like used during dental treatment.

BACKGROUND

In a dental treatment, a desired treatment may be performed by cutting a surface layer of a tooth. A medical cutting tool used during the treatment includes a shank portion gripped by a chuck of a handpiece, and a working portion continuously formed from the shank portion and including a cutting blade which is formed from an outer circumference to a leading end portion and is used to cut a surface layer. The medical cutting tool formed as described above is fixed to the handpiece when the shank portion is gripped by the chuck. Then, by an operation of a doctor, the rotating working portion is pressed to a portion to be treated, thereby cutting a desired portion.

In the medical cutting tool, the working portion needs to ensure a sufficient cutting performance with respect to a hard surface layer. Thus, in general, the working portion is formed using cemented carbide represented by tungsten carbide. The shank portion needs to ensure strength that can sufficiently resist bending and warping affected when a desired portion is cut by the working portion. When the working portion is formed using cemented carbide to improve the strength of the shank portion, it is preferable that the shank portion be formed continuously from the working portion and using cemented carbide.

However, there occurs a problem that the time used to process the cemented carbide in a shape corresponding to the medical cutting tool takes long. Thus, the shank portion is formed using, for example, SUS 420 which is martensitic stainless steel or carbon tool steels (SK), an intermediate component used to form the working portion is formed by cemented carbide, and the intermediate component of the working portion is bonded to a leading end of the shank portion by pressure welding, so that a medical cutting tool processed in a desired shape is provided.

As described above, when stainless steel or tool steel and cemented carbide are bonded to each other, an optimum method corresponding to a material to be bonded is selected and employed from methods such as pressure welding including friction pressure welding and heating pressure welding, resistance welding, and brazing in general.

SUMMARY OF INVENTION

Technical Problem

When stainless steel or carbon steel forming the shank portion and cemented carbide forming the working portion are bonded to each other using friction pressure welding, resistance welding, and brazing, a bonded portion is heated. Accordingly, a strength of a material forming the shank portion may vary due to a thermal effect, and cemented carbide may be oxidized. That is, an annealing effect may occur due to an increase in temperature of the bonded portion, and thus the strength of the shank portion may decrease and an oxide film may be generated on a surface of cemented carbide.

When a material forming the shank portion is martensitic stainless steel or carbon steel that may expect hardening from a heat treatment, the strength can be improved by performing heat treatment again after the bonding. However, martensitic stainless steel or carbon steel has problems that the generation of rust cannot be excluded and a fracture is likely to be generated when hardness is excessively increased by heat treatment.

In particular, from the viewpoint of preventing the generation of rust, it is preferable that austenitic stainless steel be used as a material of the shank portion. However, this material may not have an improved strength from heat treatment. Thus, the strength is improved by extending a structure to a fiber shape by a cold drawing process. However, when a structure extended in a fiber shape changes to a granular structure, the strength may be degraded.

An object of the invention is to provide a medical cutting tool in which rust is not be generated, a fracture is hardly generated, and a high strength is stably exhibited.

Solution to Problem

A medical cutting tool according to the invention to resolve the above problems is a medical cutting tool formed by brazing a working portion formed of cemented carbide or ceramic to a leading end of a shank portion formed by a round austenitic stainless steel bar, wherein the shank portion includes a shank, a neck formed to be continuous to the shank, and a joint which is formed to be continuous to neck and brazes the working portion formed of cemented carbide or ceramic, and at least a portion of stainless steel in the joint and near the joint of the neck includes a structure of a fiber shape.

In the medical cutting tool described above, it is preferable that a structure of the stainless steel in the joint at a side of the working portion be a granular structure.

Advantageous Effects of Invention

In the medical cutting tool according to the invention, the shank portion is formed of austenitic stainless steel, and includes the shank, the neck, and the joint, and at least a portion of stainless steel in the joint and near the joint of the neck has a structure of a fiber shape. Thus, it is possible to sufficiently resist bending or warping acting when the working portion presses and cuts a hard layer.

In addition, since the structure at the side of the working portion of stainless steel in the joint is a granular structure, the joint at the side of the working portion is in an annealing state, and thus flexibility can be exhibited and a fracture can be difficult to be generated.

REFERENCE SIGNS LIST

A Cutting tool
1 Shank portion
1a Shank
1b Neck
1c Joint
1d Brazing surface
2 Working portion
2a Cutting blade
2b Brazing surface
3 Brazing portion
5a Apex
5b Sloped surface
6 Solder
7 Material
8 Intermediate material
11 Chuck
12 Axis line
13 Holding member
13a Holding hole
14 Heating member
15 Nozzle

DESCRIPTION OF EMBODIMENTS

Hereinafter, a medical cutting tool (hereinafter, referred to as a "cutting tool") of the invention will be described. The cutting tool of the invention is fixed to a chuck of a handpiece gripped and operated by a hand of a doctor to be rotated, so that a working portion presses a surface layer of a tooth or a surface of a bone including an alveolar bone to cut the surface layer or the surface.

In particular, a favorable cutting performance is ensured by forming the working portion using cemented carbide or ceramic (hereinafter, represented by and referred to as "cemented carbide"), and at least a portion of stainless steel in a joint and near the joint of a neck forming a shank portion which is constructed by a round austenitic stainless steel bar (hereinafter, simply referred to as "stainless steel") is formed in a structure of a fiber shape, thereby exhibiting high durability.

In addition, in the cutting tool of the invention, a structure on a side of the working portion of a joint forming the shank portion is formed in a granular structure, thereby causing a side of the brazing portion in the joint to exhibit flexibility so that a fracture is hardly generated.

In the cutting tool according to the invention, the shank portion is formed using a round stainless steel bar. The shank portion includes a shank, a neck formed to be continuous to the shank, and a joint formed to be continuous to the neck. In the shank portion, at a stage of an intermediate component preceding brazing of a material of cemented carbide forming the working portion, the shank and the neck are provided in the substantially same shape and size as those of a desired cutting tool, and the joint is provided in a size corresponding to a size of a material to be brazed. The shank portion is extremely thin, where the shank which is the thickest portion is about 1.6 mm and the thinnest portion in the neck is about 0.4 mm.

The neck forming the shank portion has a function of smoothly connecting from the thickness of the shank to the thickness of the working portion (thickness of the joint). In a general cutting tool, the thickness of the shank is greater than the thickness of the working portion, and thus the neck is formed in a tapered shape where a diameter decreases from the shank to the joint.

Since a great stress acts on the neck while a desired treatment is performed, a high strength is needed to be exhibited. The strength in the neck can be identified by conducting a test such as a tensile test and a flexural test. However, the inventor verifies a relation among the Vickers hardness, the strength needed for the cutting tool, and the extension of a fiber of a structure entailed by a cold drawing process as a result of various experiments conducted in a developmental process of the cutting tool over the years.

That is, after the cold drawing process, it is verified that both a granular structure and a fiber shaped structure are included when the Vickers hardness of stainless steel is around 200, and a structure is extended in a fiber shape when the Vickers hardness is greater than or equal to 250. In addition, it is verified that it is possible to sufficiently resist bending and a warping that act on the neck when the Vickers hardness of stainless steel in the neck is greater than or equal to 350 and the working portion presses and cuts a tooth. However, it is verified that the Vickers hardness has an upper limit which is about 650 at the maximum, and in particular, it is preferable that the Vickers hardness is in the range of 350 or more and 600 or less because there occurs a problem that a fracture easily generated when the hardness is excessively high.

Accordingly, stainless steel forming the shank portion needs to be able to have the Vickers hardness in the neck in the range of 350 or more and 650 or less. For this reason, the cold drawing process is performed in advance on the stainless steel forming the shank portion, and a structure is extended in a fiber shape. In this way, by extending the structure in a fiber shape, it is possible to form at least a portion of stainless steel in the joint and near the joint of the neck in a structure of a fiber shape.

Further, the surface of the stainless steel, in which a structure is extended in a fiber shape by performing the cold drawing process, needs to have a sufficiently great value than the Vickers hardness of 350. When the surface of austenitic stainless steel has such hardness, it is possible to provide the Vickers hardness of the neck of 350 or more and the fiber shaped structure by cutting a portion corresponding to the neck in forming the shank portion.

Tungsten carbide (WC) or titanium carbide used as a cutting tool in machine processing may be employed as cemented carbide forming the working portion, and carbide ceramics represented by cermet may be employed as ceramic. The cemented carbide is brazed to the joint formed at a leading end of the shank portion in a state of a material. Thereafter, in a state in which the shank is gripped, machine processing is performed to have a size corresponding to a desired cutting tool, and machine processing of forming a spiral-shaped cutting blade is performed. Therefore, when a material of the working portion is brazed to the shank portion, the shank and the neck forming the shank portion substantially have a shape and a size corresponding to a desired cutting tool. However, a material of the joint and the working portion does not have a shape of the desired cutting tool, and has a large size.

In the invention, a material of a solder used when the joint of the shank portion and a material of the working portion are brazed is not particularly limited. However, considering an influence of a brazing temperature with respect to the shank portion, a silver solder that melts at a relatively low temperature (for example, about 700° C.) is preferable. In addition, a property of the solder is not particularly limited, and any of a foil shape, a bar shape, and a paste shape may be used. However, a solder in a paste shape is preferable since a thickness of the joint of the shank portion or a material of the working portion thin, and a void is small.

When a material of the working portion is brazed to the joint of the shank portion, typically, cemented carbide which is the material of the working portion is heated in general. In this case, examples of a scheme of heating the material of the working portion formed of cemented carbide or ceramic include a heat scheme using a flame, a heat scheme of accommodating the material in a holding furnace, a heat scheme using an electromagnetic induction, and the like, and a scheme may be selected and employed from the schemes.

In the invention, the material of the working portion is brazed to the joint forming the shank portion. Thus, due to heat given during the brazing, a temperature of the joint on the side of the working portion increases to an annealing temperature, and the temperature of the joint and the neck near the joint increases to an annealing temperature depending on a heating temperature and a heating time.

Since the structure of stainless steel forming the shank portion is extended in a fiber shape, the joint on the side of the working portion is annealed so that the structure becomes a granular structure. When the structure of the joint on the side of the working portion is a granular structure, the granular structure portion exhibits flexibility so that a fracture is hardly generated.

In particular, since the structure is stainless steel extended in a fiber shape, due to heat entailed by a brazing of cemented carbide which is a material of the working portion for the joint, both the joint and the neck are annealed, and thus a structure of a fiber shape may become a granular structure. Thus, it is preferable that a brazing region of stainless steel forming the shank portion and the neighborhood be forcibly cooled down.

As described above, by forcibly cooling down the brazing region of stainless steel including the structure extended in a fiber shape while performing brazing, it is possible to prevent the temperature of the shank portion including the joint from excessively increasing.

Accordingly, the structure of the fiber shape in the neck can be maintained, and the strength of the neck can be maintained.

Next, an overall configuration of the cutting tool according to the embodiment will be described with reference to FIG. 1.

Figure 1:
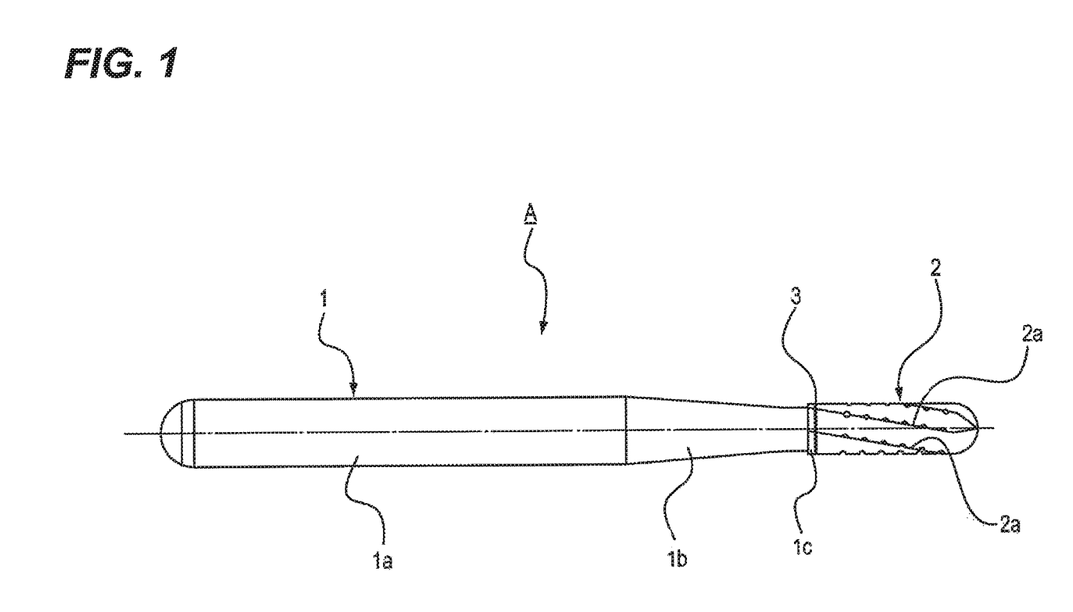
FIG. 1 is a diagram illustrating a configuration of a cutting tool.

Referring to FIG. 1, a cutting tool A includes a shank portion 1 fixed to a chuck of a handpiece (not illustrated), and a working portion 2 that cuts a surface layer of a tooth (not illustrated). The shank portion 1 is made from stainless steel in which a structure is extended in a fiber shape, and the working portion 2 is made from WC as a material. The cutting tool A is constructed when the shank portion 1 and the working portion 2 are connected and integrated with each other through a brazing portion 3 using brazing.

The shank portion 1 of the cutting tool A is fixed to the chuck of the handpiece (not illustrated), and rotates in this state. For this reason, a shank 1a fixed to the chuck of the handpiece is formed on one side of the shank portion 1. The shank 1a has a constant thickness (a thickness of about 1.6 mm in the embodiment) corresponding to the size of the chuck regardless of the shape, the thickness, and the length of the working portion 2.

A specification such as an external shape, a thickness, and a length of the working portion 2 in the cutting tool A is set according to a therapeutic purpose of a portion or a degree to be cut. Thus, the cutting tool A illustrated in FIG. 1 is merely an example of the cutting tool A. For example, a shape of the working portion 2 includes a round bar shape illustrated in FIG. 1 in which a leading end has a spherical shape and a thickness is uniform, a tapered shape in which a leading end has a spherical shape and a thickness becomes thinner toward the leading end, a sphere shape, and the like. A plurality of spiral-shaped cutting blades 2a is formed on an outer circumference surface of the working portion 2.

Figure 2:
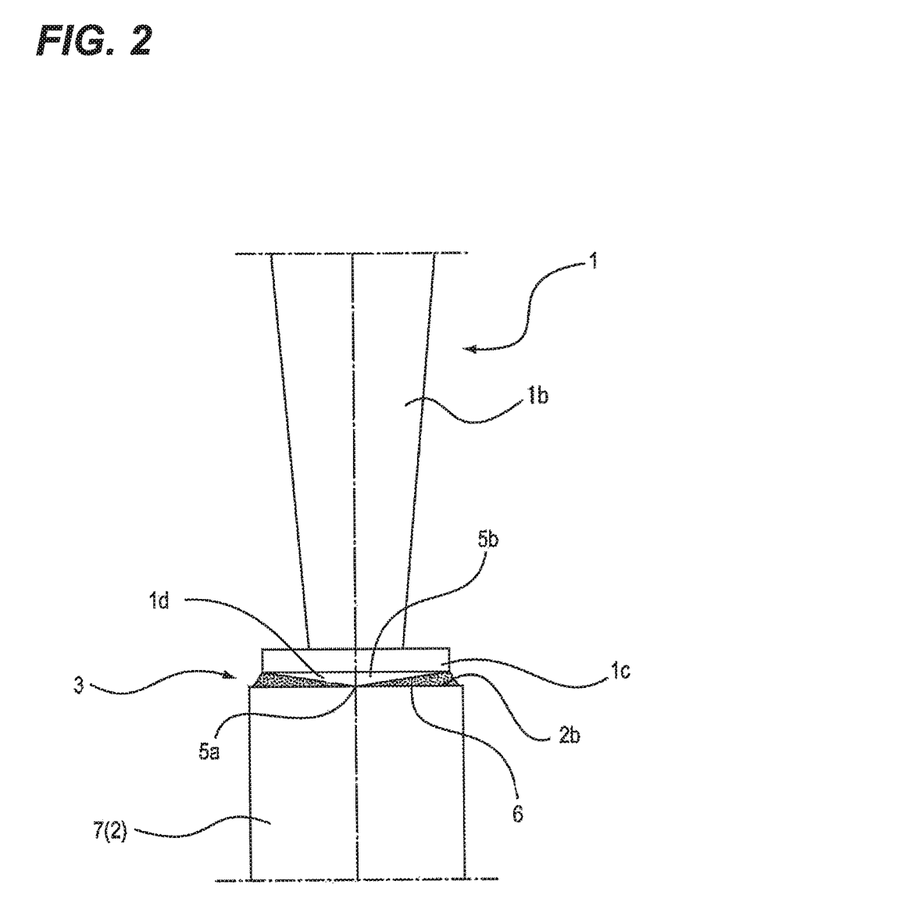
FIG. 2 is an enlarged view illustrating a state in which a material of a working portion is brazed to a brazing surface of a shank portion.
Figure 4:
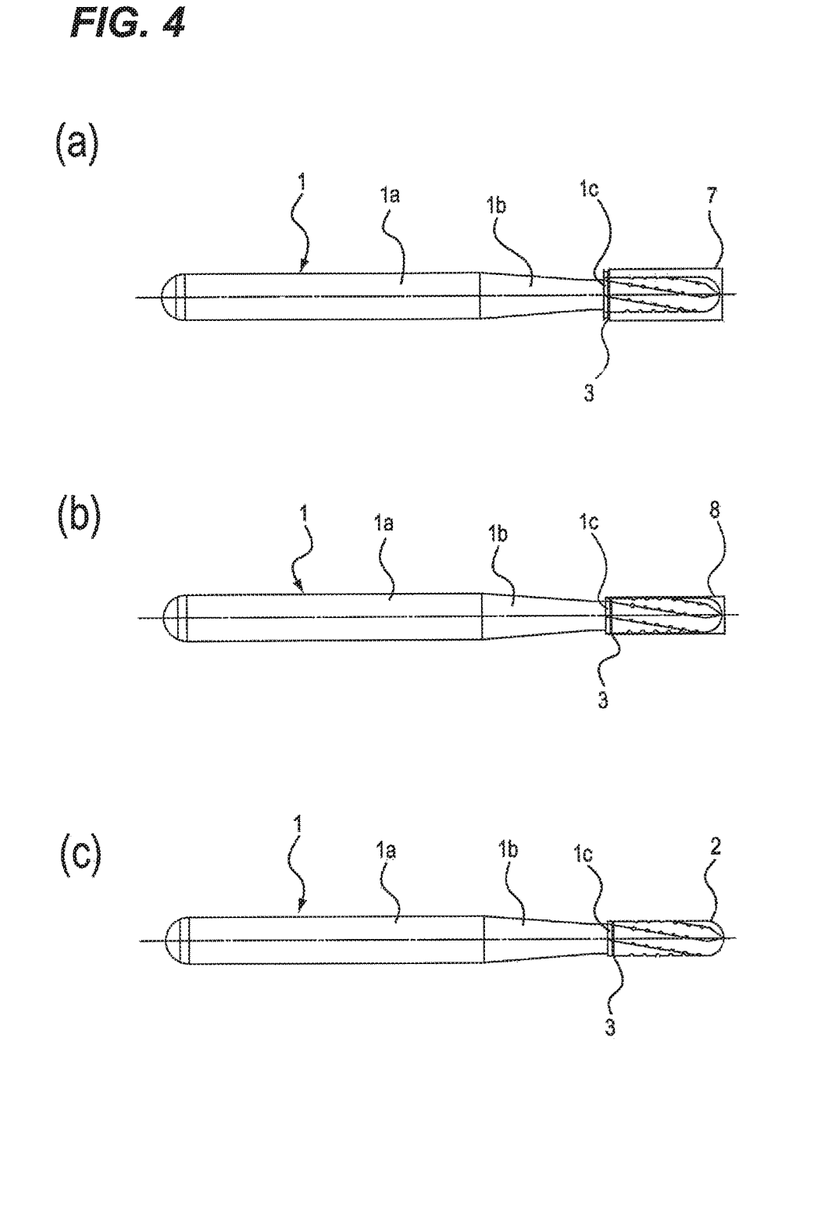
FIG. 4 is a diagram illustrating a process order when the cutting tool is manufactured.

As described above, an external diameter of the working portion 2 is set to various values corresponding to the purpose of the cutting tool A. Thus, as illustrated in FIGS. 2 and 4, a material 7 of cemented carbide used to form the working portion 2 corresponding to the cutting tool A (hereinafter, simply referred to as "material 7") is brazed to the leading end of the shank portion 1 corresponding to the desired cutting tool A in advance, and then machine processing such as cutting and grinding is performed on the leading end portion of the shank portion 1 and the material 7, thereby providing a shape and a size corresponding to the desired working portion 2.

Thus, in the shank portion 1, a neck 1b in a tapered shape is formed to be continuous to the shank 1a having a constant thickness, and a joint 1c having a diameter substantially equal to or slightly less than a thickness of the material 7 is formed at a leading end of the neck 1b. A thickness of the joint 1c is not particularly limited, and one third of a diameter of the joint 1c or less is sufficient for the thickness. As illustrated in FIG. 2, a brazing surface 1d is formed on an edge face of the joint 1c, and a sloped surface 5b having an apex 5a is formed on the brazing surface 1d.

The sloped surface 5b having the apex 5a formed on the brazing surface 1d of the shank portion 1 is formed as a sloped surface having a circular cone shape for an easiness of processing. By forming the sloped surface 5b in a circular cone shape, the brazing surface 1d may be fabricated concurrently with a fabrication of another portion, for example, the neck 1b and the joint 1c when the shank portion 1 is rotated and cut from a stainless steel material having a round bar shape, which is advantageous.

As a result of various experiments conducted by the inventor, as one of conditions for being able to exhibit a practical bending strength by the brazing portion 3, a relation between a height of the sloped surface 5b in the brazing portion 3 and a thickness of the brazing portion 3 is confirmed to be present. That is, referring to the relation, it is preferable that the height of the sloped surface 5b be set in the range of 0.5% to 8% of the diameter of the brazing surface. When the height is less than a value in the range, an amount of solder is small, and thus the sufficient joint strength is difficult to be obtained. In addition, when the height is greater than a value in the range, an amount of solder is large, and thus workability deteriorates, cost increases, and variation occurs in a joint strength. In particular, to obtain a uniform and sufficiently great joint strength, it is preferable that the height of the sloped surface 5b provided on the brazing surface 1d be set in the range of 1% to 5% of a diameter of the brazing surface 1d.

For this reason, in a case of the cutting tool A in which the thickness of the working portion 2 is 1.2 mm, the height of the sloped surface 5b is 0.038 mm, and is set to be about 3.1% of the thickness of the working portion 2. In addition, in a case of the cutting tool A in which the thickness of the working portion 2 is 1.0 mm, the height is 0.031 mm, and is set to be about 3.1% of the thickness of the working portion 2. Further, in a case of the cutting tool A in which the thickness of the working portion 2 is 0.8 mm, the height is 0.022 mm, and is set to be about 2.8% of the thickness of the working portion 2.

In addition, the brazing surface 2b is formed on an edge face at the side of the shank portion 1 of the working portion 2 (material 7). The shape of the brazing surface 2b is not particularly limited, and may be a flat surface or the same shape as that of the brazing surface 1d of the shank portion 1. In the embodiment, as illustrated in FIG. 2, the brazing surface 2b of the working portion 2 is formed as a flat surface.

The shank portion 1 and the material 7 are disposed in which the brazing surface 1d formed at the joint 1c of the shank portion 1 and the brazing surface 2b formed on an edge face of the material 7 face each other in the brazing portion 3, and are bonded to each other by the solder 6 supplied to a void formed between the brazing surfaces 1d and 2b and hardened.

In particular, by causing the apex 5a of the sloped surface 5b formed on the brazing surface 1d of the shank portion 1 to come into contact with the brazing surface 2b of the material 7, the void between the brazing surfaces 1d and 2b is set to a size identical to the height of the sloped surface 5b. Accordingly, a volume of the void in the brazing portion 3 is substantially constant, and a supplied amount of the solder 6 may be stable.

When the shank portion 1 and the material 7 are brazed and bonded to each other, the brazing portion 3 is heated to a melting temperature of the solder 6, and the solder 6 is melted due to an increased temperature in the brazing portion 3, so that the void formed between the brazing surfaces 1d and 2b is filled. Then, when heating of the brazing portion 3 is suspended, the brazing portion 3 is cooled down, and the solder 6 is hardened, so that the shank portion 1 and the material 7 are bonded to each other. Thereafter, the cutting tool A is constructed by performing predetermined machine processing on the material 7.

In the cutting tool A constructed as described above, the neck 1b has the hardness greater than or equal to the Vickers hardness 350, and it is possible to exhibit the sufficient strength with respect to the bending stress and the torsional force acting when a desired cutting operation is performed by the working portion 2.

For example, when the Vickers hardness of the neck 1b is less than or equal to 350, the neck portion is bent, and a stable cutting is difficult, which is not preferable. However, an unlimitedly high hardness of the neck 1b is not preferable. For example, when the Vickers hardness exceeds 650, a fracture is easily generated, which is not preferable.

Next, a procedure of manufacturing the cutting tool A constructed as described above will be described. In the embodiment, while a brazing operation is performed, a neighborhood of the brazing region is forcibly cooled down, thereby preventing an annealing of the neck 1b in the shank portion 1 to maintain a structure extended in a fiber shape, and maintaining the Vickers hardness greater than or equal to 350.

In the embodiment, the joint 1c and a joint part between the joint 1c and the neck 1b are collectively referred to as a brazing region. In addition, a neighborhood of the joint 1c in the neck 1b includes the joint part between the joint 1c and the neck 1b, is a portion included in a neighborhood of the brazing region, and is a portion about twice a thickness of the joint 1c.

When the material 7 of the working portion 2 is brazed to the shank portion 1 formed from stainless steel, a scheme of cooling down the brazing region and the neighborhood of the brazing region are not particularly limited. A cooling scheme that may maintain the brazing region and the neighborhood of the brazing region at a temperature less than or equal to a transformation temperature of a structure may be used. That is, a transformation of austenitic stainless steel may occur from about 500° C., and thus a cooling scheme that may maintain the temperature or less by forcibly cooling down the brazing region and the neighborhood of the brazing region in the shank portion 1 may be employed.

Examples of the cooling scheme include a cooling scheme that sprays gas having a pressure, a cooling scheme that sprays liquid as a mist, a cooling scheme that directly sprays liquid, a cooling scheme that sprays a dry ice chip or an ice chip, and a cooling scheme that disposes a cooling medium at the brazing region and the neighborhood of the brazing region, and sprays wind through the cooling medium. A cooling scheme may be selected and employed from the cooling schemes.

In addition, when the shank portion 1 is formed using stainless steel, and the working portion 2 is formed using cemented carbide which is formed from WC, it is preferable that an oxidization of a surface of the stainless steel and a surface of the cemented carbide occurring during a brazing operation be reduced as possible. For this reason, it is preferable that an inert gas be sprayed when forcibly cooling down the brazing region or the neighborhood of the brazing region in stainless steel.

In this case, it is preferable that gas generally used as an inert gas such as nitrogen gas and argon gas be used as the inert gas. However, an object of spraying an inert gas is to prevent an oxidization of a surface of stainless steel and a surface of cemented carbide, and thus gas which is inert at a degree capable of achieving the object may be used. That is, 100% nitrogen gas or argon gas may not be used as an inert gas, and gas in which nitrogen gas or argon gas and air are mixed may be used.

In addition, when the shank portion 1 and the material 7 of the working portion 2 are brazed, gas is generated due to an increased temperature of a solder. Thus, as an example of the embodiment, by forming the sloped surface, 5b including the apex 5a on the brazing surface 1d formed on the edge face of the joint 1c of the shank portion 1, the generated gas may be smoothly removed from a brazing part In particular, when a brazing operation is performed, by causing the apex 5a to come into contact with the edge face of the material 7, a gap therebetween may be maintained.

Further, when the shank portion 1 and the material 7 of the working portion 2 are brazed, it is preferable that cemented carbide forming the material 7 be disposed in the bottom for supporting, and the shank portion 1 be substantially perpendicularly disposed to cause the apex 5a to come into contact with the edge face of the material 7. When disposed in this position, gas generated during a brazing rises along the sloped surface 5b and is vented to atmosphere from an outer circumference of the joint 1c. In addition, a melted solder penetrates into a small part by capillary phenomenon acting on a minute void formed from a slope of the protrusion portion and the edge face of the working portion, and an excellent brazing may be realized.

By providing the sloped surface 5b including the apex 5a on the brazing surface 1d of the shank portion 1, a gap between the brazing surface 1d and the edge face of the material 7 (brazing surface) may be set during a brazing operation, and the gap may be maintained through the brazing operation. Thus, the brazing operation may be performed while the gap between the brazing surface 1d and the edge face of the material 7 is stably maintained, and a variation in strength resulting from the brazing operation may be excluded.

A shape of the sloped surface 5b including the apex 5a provided on the brazing surface 1d is not particularly limited. Examples of the shape include a curved surface shape, a circular cone shape, a pyramid shape, and the like, and a shape including the shapes may be used. However, considering at least a condition of easiness and the like of processing when the shank portion 1 is formed, it is preferable to be formed as a circular cone shape.

The sloped surface 5b including the apex 5a provided on the brazing surface 1d of the shank portion 1 is brazed in a state of coming into contact with an opposing brazing surface (the edge face of the material 7). Thus, a height of the sloped surface 5b defines a gap between two opposing brazing surfaces, and sets a volume of a solder in the brazing portion. For this reason, it is preferable that the height of the sloped surface 5b be changed in response to the thickness in the joint portion between the shank portion 1 and the working portion 2.

A configuration of a brazing device suitably used when the shank portion 1 and the material 7 forming the working portion 2 are brazed as described above, and a procedure of a brazing using the brazing device will be described with reference to FIG. 3. The brazing device illustrated in FIG. 3 is configured so as to be able to forcibly cool down a brazing region of the shank portion 1 and the material 7, and a neighborhood of the brazing region by spraying an inert gas.

Figure 3:
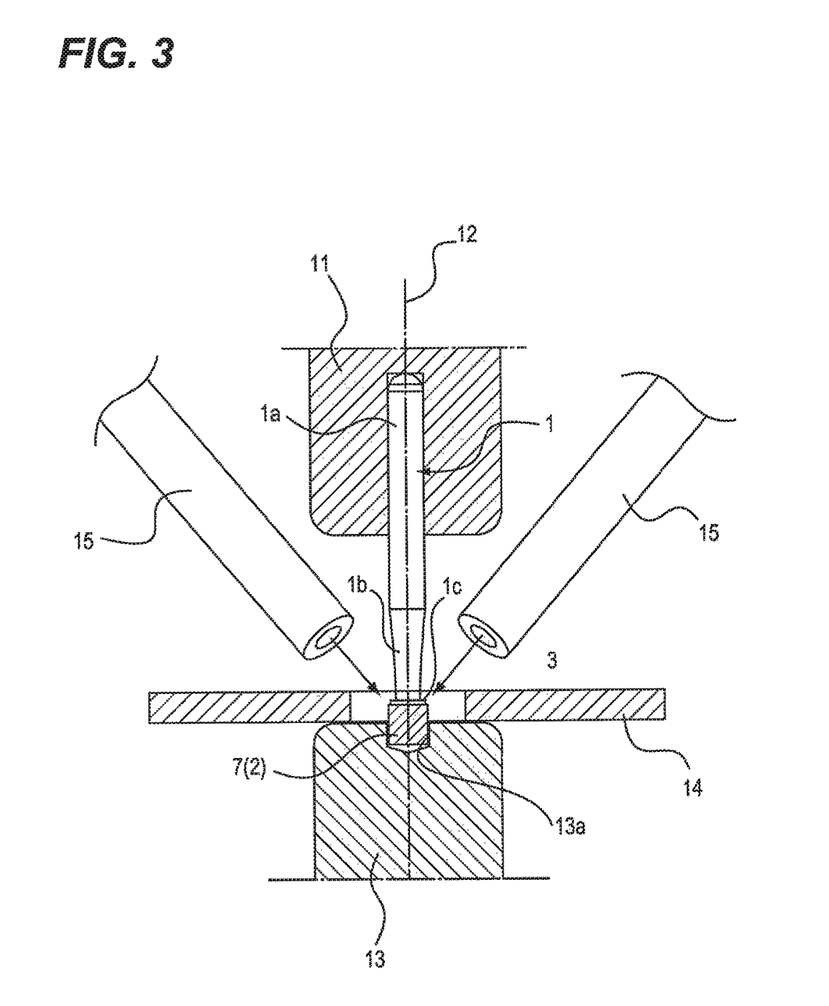
FIG. 3 is a diagram illustrating a configuration in which gas is sprayed to a brazing region and near the brazing region to perform cooling.

Referring to FIG. 3, a chuck 11 is configured to be able to reciprocate along an axis line 12 by gripping the shank 1a of the shank portion 1. A holding member 13 is configured to be able to put and hold the material 7 of the working portion 2 in a holding hole 13a formed on the axis line 12. A heating member 14 is configured to be able to heat the material 7 held in the holding hole 13a of the holding member 13 by a coil in a ring shape.

A nozzle 15 is configured to spray an inert gas to forcibly cool down a brazing region of the brazing surface 1d formed at the joint 1c of the shank portion 1 and the material 7 of the working portion, and a neighborhood of the brazing region. As the inert gas sprayed from the nozzle 15, nitrogen gas, argon gas, and the like may be selectively used. For this reason, a source of supply of an inert (not illustrated) is connected to the nozzle 5.

The number of nozzles 15 is not limited, and may be one, or two or more. The nozzle 15 is needed to be disposed to be able to evenly cool down a brazing region in the shank portion 1 and the neck 1b which is a neighborhood of the brazing region. In addition, a temperature of an inert gas sprayed from the nozzle 15 is not limited, and a sufficient cooling effect may be exhibited even when an inert gas in a normal temperature state is sprayed.

An amount of inert gas sprayed from the nozzle 15 is preferably large. However, it is preferable to be appropriately set from a relation with a scheme of heating the brazing portion 3. For example, in a case of a heating scheme using a combustion flame of gas, a stable combustion flame may be difficult to be formed when a flow rate of an inert gas increases, and a current speed increases. However, in a case of a scheme using an induction heating as an example of the embodiment, a high cooling effect may be exhibited by spraying an inert gas of a sufficiently large flow rate.

As illustrated in FIGS. 2 and 3, first, the material 7 is put into the holding hole 13a of the holding member 13, and the shank 1a of the shank portion 1 is gripped by the chuck 11. The solder 6 is supplied to the brazing surface 2b which is the edge face of the material 7, the chuck 11 is caused to descend along the axis line 12, and the apex 5a of the sloped surface 5b formed on the brazing surface 1d of the shank portion 1 is caused to come into contact with the brazing surface 2b.

When an inert gas is sprayed from the nozzle 15 by maintaining the state, the brazing region in the shank portion 1 and the neck 1b which is a neighborhood of the brazing region are cooled Further, the material 7 of the working portion 2 is heated for a short period of time by operating the heating member 14, and the solder 6 is melted due to the heating to flow to and fill the void formed by the sloped surface 5b provided on the brazing surface 1d of the shank portion 1, and the edge face of the material 7. In addition, gas generated due to the melting of the solder 6 moves upward along the sloped surface 5b, arrives at the circumference surface of the joint 1c, and then is vented to atmosphere.

The heating member 14 is operated for a predetermined time (for example, about greater than or equal to 1 second and less than or equal to 5 seconds), and the operation of the heating member 14 is suspended after the melted solder 6 sufficiently flows to fill the void formed by the sloped surface 5b and the edge face of the material 7. The solder 6 is hardened due to the suspension of the operation of the heating member 14, and a brazing operation is ended.

As described in the foregoing, while the heating member 14 is operated, and the brazing operation is performed, an inert gas is sprayed to the brazing region in the shank portion 1 and the neck 1b which is a neighborhood of the brazing region to forcibly cool down the brazing region and the neck 1b. For this reason, even though heat entailed by the brazing is transferred to the neck 1b, an increase in temperature may be inhibited, and recrystallization of a structure extended in a fiber shape may be prevented. Since a structure of the neck 1b maintains a state of being extended in a fiber shape, the Vickers hardness of 350 or more is maintained, and a strength as the cutting tool A may be maintained.

As describe above, the material 7 of the working portion 2 brazed to the shank portion 1 may not have a shaft center accurately matching a shaft center of the shank portion 1. For this reason, as illustrated in FIG. 4, the desired cutting tool A is manufactured by performing machine processing including a cutting or a grinding on the material 7.

That is, as illustrated in FIG. 4(a), the material 7 of cemented carbide sufficiently greater than a thickness and a length of the desired working portion 2 is brazed to the brazing surface 1d formed at the joint 1c of the shank portion 1, and then an intermediate material 8 is constructed by processing the material 7 as illustrated in FIG. 4(b). This operation is fixing the shank 1a of the shank portion 1 to a processing equipment (not illustrated), and grinding the material 7 so that the working portion 2 has a desired thickness while causing a rotation in this state. As described above, since a center of rotation of the shank 1a of the shank portion 1 is a center of rotation of the cutting tool A, a center of rotation of the intermediate material 8 accurately matches the center of rotation of the shank portion 1 even when a center of rotation of the material 7 does not match the center of rotation of the shank portion 1.

Next, as illustrated in FIG. 4(c), the intermediate material 8 is processes to form a hemispherical edge, and the spiral-shaped cutting blades 2a are formed on a circumference surface. Through the processing, the working portion 2 is formed of the material 7 through the intermediate material 8, thereby manufacturing the desired cutting tool A.

The inventors measured the Vickers hardness of the neck 1b in the cutting tool A formed by forcibly cooling down the brazing region in the shank portion 1 and the neck 1b which is a neighborhood of the brazing region, and the Vickers hardness of the neck 1b in a cutting tool formed without forcibly cooling down the neck 1b, and compared the Vickers hardness. The result will be described.

Figure 5:
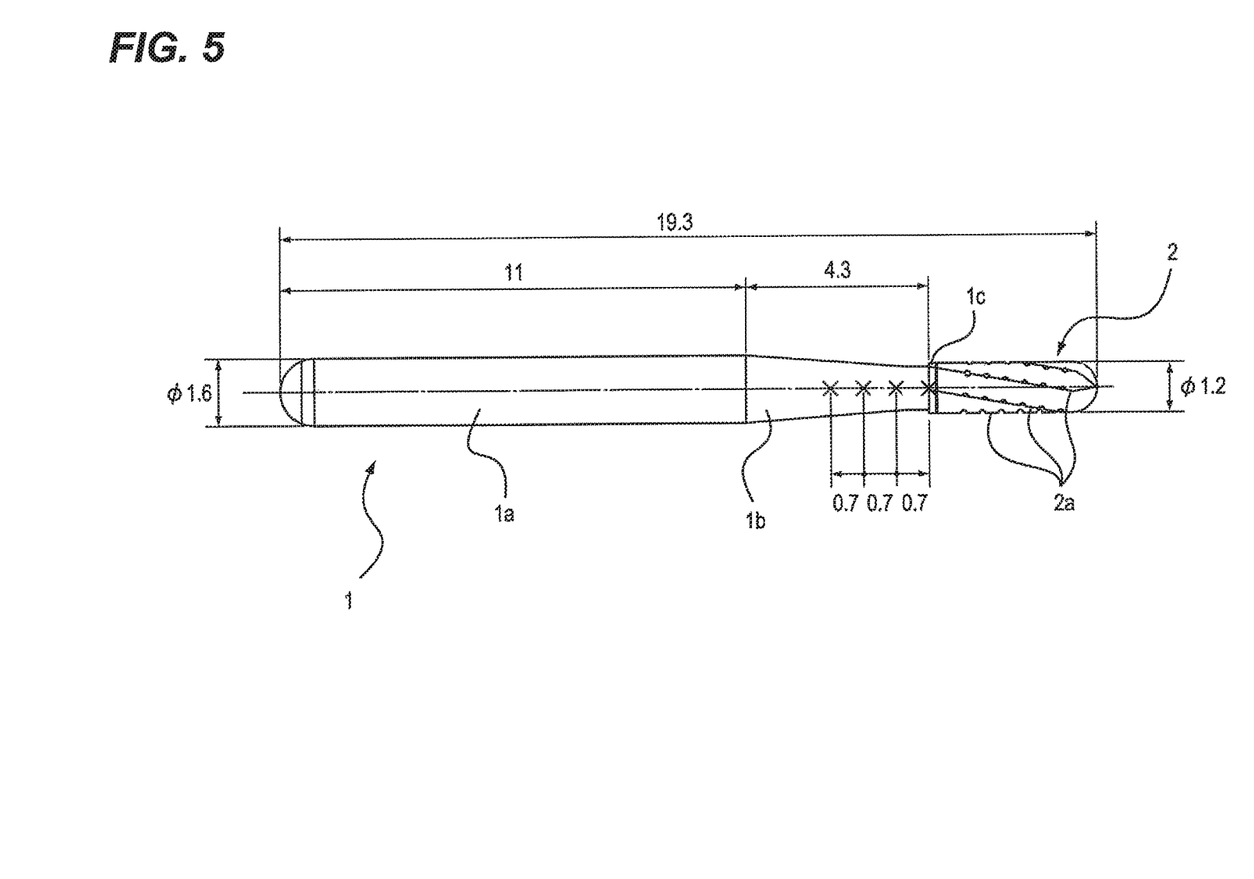
FIG. 5 is a diagram illustrating a measurement position of hardness in a neck of the cutting tool.

Ten cutting tools of a specification illustrated in FIG. 5 are fabricated as test pieces. A minimum size of the neck 1b in FIG. 5 is 1.02 mm. Five test pieces among the ten test pieces are fabricated by spraying nitrogen gas of 5 normal liters per minute to the brazing region in the shank portion 1 and a neighborhood of the brazing region, and forcibly cooling down the brazing region and the neighborhood. The remaining five pieces are fabricated without being cooled down.

As a brazing region in each test piece, an intersection part of the neck 1b and the joint 1c of the shank portion 1 is set, and the hardness is measured for four points (0, 0.7, 1.4, and 2.1) from this part for each 0.7 mm. A measurement scheme of hardness is based on JIS 2244 (2003). The Vickers hardness is HV0.3, a test pressure is 2.942 N, and a holding time of the test pressure is 15 seconds.

As a result of the test, the Vickers hardness of the five cooled pieces is in a range of 367 to 412 at the point 0, in a range of 475 to 503 at the point 0.7, in a range of 504 to 533 at the point 1.4, and in a range of 516 to 550 at the point 2.1. In addition, the Vickers hardness of the five pieces that are not cooled is in a range of 285 to 299 at the point 0, in a range of 334 to 343 at the point 0.7, in a range of 439 to 453 at the point 1.4, and in a range of 484 to 508 at the point 2.1.

From a result of the test, it is clarified that the Vickers hardness of 350 or more of the neck 1b may be realized by forcibly cooling down the brazing region and a neighborhood of the brazing region. In the neck 1b having the Vickers hardness of 350 or more, it can be presumed that a structure maintains a state of being extended in a fiber shape.

In addition, ten cutting tools in which a length of the neck 1b of FIG. 5 is 6.3 mm, and a minimum size of the neck 1b is 0.62 mm are fabricated as test pieces. Similarly to the above test, five test pieces among the ten test pieces are fabricated by spraying nitrogen gas of 5 normal liters per minute to the brazing region in the shank portion 1 and a neighborhood of the brazing region, and forcibly cooling down the brazing region and the neighborhood. The remaining five pieces are fabricated without being cooled down. Then, the hardness for four points are measured under the same condition as described above.

As a result of the test, the Vickers hardness of the five cooled pieces is in a range of 357 to 376 at the point 0, in a range of 460 to 478 at the point 0.7, in a range of 533 to 544 at the point 1.4, and in a range of 550 to 558 at the point 2.1. In addition, the Vickers hardness of the five pieces that are not cooled is in a range of 260 to 283 at the point 0, in a range of 318 to 342 at the point 0.7, in a range of 404 to 430 at the point 1.4, and in a range of 502 to 532 at the point 2.1.

From the result of the test, it is clarified that the Vickers hardness of 350 or more of the neck 1b may be realized by forcibly cooling down the brazing region and a neighborhood of the brazing region even for the cutting tool in which a length of the neck 1b is 6.3 mm, and a minimum size of the neck 1b is 0.62 mm. In the neck 1b having the Vickers hardness of 350 or more, it may be presumed that a structure maintains a state of being extended in a fiber shape.

Figure 6:
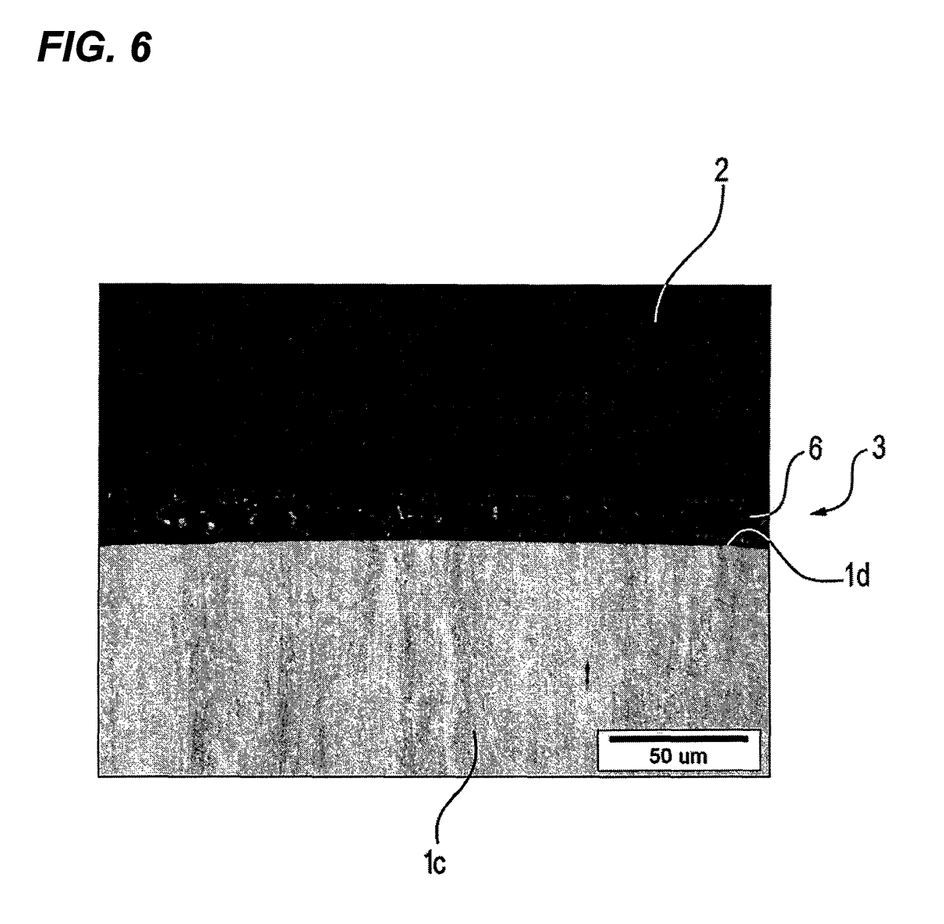
FIG. 6 is a diagram illustrating a structure of the brazing region of the cutting tool.

In the cutting tool A formed as described above, the joint 1c forming the shank portion 1 at the side of the working portion is in a granular structure. FIG. 6 is an enlarged view of the structure of the brazing portion 3 in a longitudinal direction (a direction that cuts the shank portion 1, the solder, and the working portion 2 longitudinally) of the cutting tool A. The joint 1c at the side of the working portion 2 is in a granular structure at a range of a depth of several μm, and another portion maintains a structure of a fiber shape.

INDUSTRIAL APPLICABILITY

A cutting tool of the invention is formed by brazing and bonding a working portion formed of cemented carbide or ceramics to a leading end of a shank portion formed by a round austenitic stainless steel bar, and at least a portion of stainless steel in a joint and near the joint of the neck includes a structure of a fiber shape, and thus the neck has a sufficient strength for a bending and a warping. For this reason, it is advantageous to be used when cutting a hard layer such as a tooth.

The invention claimed is:

1. A method of producing a medical cutting tool having a working portion formed of cemented carbide or ceramics, a shank portion formed by a round austenitic stainless steel bar, the shank portion including a shank, a neck formed to be continuous to the shank and a joint portion which is formed to be continuous to the neck, the joint portion being of a cylindrical shape having a diameter, the neck including stainless steel, the joint portion including stainless steel, the stainless steel of the neck being of a fiber structure, the neck having a first diameter and a second diameter, the first diameter of the neck at a position where the neck is connected to the shank being greater than the second diameter of the neck at a position where the neck is connected to the joint portion and the second diameter of the neck being less than the diameter of the joint portion, the method comprising the steps of:
brazing the working portion to the joint portion; and
cooling down a brazing region between the working portion and the joint portion such that the stainless steel of the joint portion transitions from a granular structure to the fiber structure in a direction from the working portion to the neck and that the neck maintains a Vickers hardness in the range of 350 -600.

2. The method of producing a medical cutting tool according to claim 1, wherein:
the step of cooling down the brazing region includes the step of spraying an inert gas to the brazing region.

3. The method of producing a medical cutting tool according to claim 2, wherein:
the inert gas includes nitrogen gas.

4. The method of producing a medical cutting tool according to claim 2, wherein:
the inert gas includes argon gas.

5. The method of producing a medical cutting tool according to claim 1, wherein:
the step of cooling down the brazing region includes the step of spraying liquid to the brazing region.

6. The method of producing a medical cutting tool according to claim 1, wherein:

the step of cooling down the brazing region includes the step of spraying dry ice chips or ice chips to the brazing region.

7. The method of producing a medical cutting tool according to claim 1, wherein:
the step of cooling down the brazing region includes the steps of:
disposing a cooling medium at the brazing region; and
spraying air to the cooling medium.

8. The method of producing a medical cutting tool according to claim 1,
while the brazing the working portion is performed, the cooling down the brazing region is performed.

* * * * *